(12) United States Patent
Lindh et al.

(10) Patent No.: US 7,899,534 B2
(45) Date of Patent: *Mar. 1, 2011

(54) EXPERT SYSTEM AND METHOD

(75) Inventors: Par Lindh, Little Canada, MN (US);
James Kalgren, Lino Lakes, MN (US);
Jeffrey E. Stahmann, Ramsey, MN (US); Rene H. Wentkowski, Overijse (BE)

(73) Assignee: Cardiac Pacemakers, Inc., St. Paul, MN (US)

( * ) Notice: Subject to any disclaimer, the term of this patent is extended or adjusted under 35 U.S.C. 154(b) by 1079 days.

This patent is subject to a terminal disclaimer.

(21) Appl. No.: 11/624,035

(22) Filed: Jan. 17, 2007

(65) Prior Publication Data

US 2007/0250125 A1 Oct. 25, 2007

Related U.S. Application Data

(63) Continuation of application No. 09/748,791, filed on Dec. 26, 2000, now Pat. No. 7,181,285.

(51) Int. Cl.
*A61N 1/362* (2006.01)
(52) U.S. Cl. .............................. 607/25; 607/9
(58) Field of Classification Search .................. 607/4, 5, 607/7, 9, 11, 17, 30, 25; 600/516
See application file for complete search history.

(56) References Cited

U.S. PATENT DOCUMENTS

| | | | |
|---|---|---|---|
| 4,712,179 A | 12/1987 | Heimer | |
| 4,809,697 A | 3/1989 | Causey, III et al. | |
| 4,825,869 A | 5/1989 | Sasmor et al. | |
| 4,928,688 A | 5/1990 | Mower | |
| 5,097,831 A | 3/1992 | Lekholm | |
| 5,174,289 A | 12/1992 | Cohen | |
| 5,226,413 A | 7/1993 | Bennett et al. | |
| 5,251,626 A | 10/1993 | Nickolls et al. | |
| 5,267,560 A | 12/1993 | Cohen | |

(Continued)

FOREIGN PATENT DOCUMENTS

WO WO-0041765 7/2000

(Continued)

OTHER PUBLICATIONS

Hall, Jeffrey A., et al., "Recordable Macros for Pacemaker Follow-Up", U.S. Appl. No. 10/348,191, filed Jan. 21, 2003, 17 pgs.

(Continued)

*Primary Examiner* — George R Evanisko
(74) *Attorney, Agent, or Firm* — Schwegman, Lundberg & Woessner, P.A.

(57) ABSTRACT

A medical device programmer and a method of operation in which a first data value is received and used in the execution of one or more algorithms. One or more suggested pulse generator settings are calculated from the one or more algorithms based on the first data value, and the one or more suggested pulse generator settings are displayed on an interactive display screen of the medical device programmer. In one embodiment, the first data value is a duration interval of a QRS complex. From the duration interval, suggestions are made as to one or more ventricular chambers in which to provide pacing pulses. Additionally, pacing intervals for an AV delay are suggested based on measured P-R intervals, or pacing intervals for an LV offset are suggested based on a measured duration interval of a V-V-interval between a right ventricular event and a left ventricular event.

18 Claims, 9 Drawing Sheets

U.S. PATENT DOCUMENTS

| | | | |
|---|---|---|---|
| 5,282,838 A | 2/1994 | Hauser et al. | |
| 5,292,341 A | 3/1994 | Snell | |
| 5,321,618 A | 6/1994 | Gessman | |
| 5,372,607 A * | 12/1994 | Stone et al. | 607/30 |
| 5,421,830 A | 6/1995 | Epstein et al. | |
| 5,431,691 A | 7/1995 | Snell et al. | |
| 5,456,952 A | 10/1995 | Garza et al. | |
| 5,487,752 A | 1/1996 | Salo et al. | |
| 5,507,782 A | 4/1996 | Kieval et al. | |
| 5,540,727 A | 7/1996 | Tockman et al. | |
| 5,549,654 A | 8/1996 | Powell | |
| 5,594,638 A | 1/1997 | Iliff | |
| 5,607,460 A | 3/1997 | Kroll et al. | |
| 5,630,835 A | 5/1997 | Brownlee | |
| 5,690,690 A | 11/1997 | Nappholz et al. | |
| 5,693,076 A | 12/1997 | Kaemmerer | |
| 5,697,959 A | 12/1997 | Poore | |
| 5,713,937 A | 2/1998 | Nappholz et al. | |
| 5,716,382 A | 2/1998 | Snell | |
| 5,792,203 A | 8/1998 | Schroeppel | |
| 5,800,473 A | 9/1998 | Faisandier | |
| 5,817,137 A | 10/1998 | Kaemmerer | |
| 5,833,623 A | 11/1998 | Mann et al. | |
| 5,891,178 A | 4/1999 | Mann et al. | |
| 5,911,132 A | 6/1999 | Sloane | |
| 6,016,442 A | 1/2000 | Hsu et al. | |
| 6,070,101 A | 5/2000 | Struble et al. | |
| 6,091,990 A | 7/2000 | Hsu et al. | |
| 6,129,744 A | 10/2000 | Boute | |
| 6,141,586 A | 10/2000 | Mower | |
| 6,148,234 A | 11/2000 | Struble | |
| 6,168,563 B1 | 1/2001 | Brown | |
| 6,249,705 B1 | 6/2001 | Snell | |
| 6,272,377 B1 * | 8/2001 | Sweeney et al. | 600/515 |
| 6,280,389 B1 | 8/2001 | Ding et al. | |
| 6,285,907 B1 | 9/2001 | Kramer et al. | |
| 6,304,773 B1 | 10/2001 | Taylor et al. | |
| 6,351,675 B1 | 2/2002 | Tholen et al. | |
| 6,370,427 B1 | 4/2002 | Alt et al. | |
| 6,400,982 B2 | 6/2002 | Sweeney et al. | |
| 6,411,847 B1 | 6/2002 | Mower | |
| 6,442,432 B2 | 8/2002 | Lee | |
| 6,442,433 B1 | 8/2002 | Linberg | |
| 6,497,655 B1 | 12/2002 | Linberg et al. | |
| 6,526,313 B2 | 2/2003 | Sweeney et al. | |
| RE38,119 E | 5/2003 | Mower | |
| 6,564,104 B2 | 5/2003 | Nelson et al. | |
| 6,622,040 B2 * | 9/2003 | Ding et al. | 607/9 |
| 6,668,194 B2 | 12/2003 | VanHout | |
| 6,669,631 B2 | 12/2003 | Norris et al. | |
| 6,999,815 B2 * | 2/2006 | Ding et al. | 607/9 |
| 7,003,349 B1 | 2/2006 | Andersson et al. | |
| 7,070,562 B2 | 7/2006 | Bardy | |
| 7,136,707 B2 | 11/2006 | Hall et al. | |
| 7,181,285 B2 * | 2/2007 | Lindh et al. | 607/30 |
| 7,383,088 B2 | 6/2008 | Spinelli et al. | |
| 7,546,162 B2 * | 6/2009 | Ding et al. | 607/30 |
| 2001/0031997 A1 | 10/2001 | Lee | |
| 2001/0039375 A1 | 11/2001 | Lee et al. | |
| 2001/0039503 A1 | 11/2001 | Chan et al. | |
| 2002/0016550 A1 | 2/2002 | Sweeney et al. | |
| 2002/0120311 A1 | 8/2002 | Lindh et al. | |
| 2002/0123672 A1 | 9/2002 | Christophersom et al. | |
| 2003/0050803 A1 | 3/2003 | Marchosky | |
| 2003/0088290 A1 | 5/2003 | Spinelli et al. | |
| 2004/0122487 A1 | 6/2004 | Hatlestad et al. | |
| 2004/0133080 A1 | 7/2004 | Mazar et al. | |
| 2004/0133246 A1 | 7/2004 | Ding et al. | |
| 2004/0143304 A1 | 7/2004 | Hall et al. | |
| 2008/0077031 A1 | 3/2008 | Spinelli et al. | |
| 2009/0248104 A1 | 10/2009 | Ding et al. | |

FOREIGN PATENT DOCUMENTS

| | | |
|---|---|---|
| WO | WO-0041766 | 7/2000 |

OTHER PUBLICATIONS

Mower, Morton, search results for U.S. Appl. No. 10/214,474, filed Aug. 8, 2002, entitled "*Method and Apparatus for Treating Hemodynamic Disfunction*", 3.

"U.S. Appl. No. 09/738,407, Final Office Action mailed Jan. 14, 2003", 6 pgs.

"U.S. Appl. No. 09/738,407, Non-Final Office Action mailed Aug. 23, 2002", 6 pgs.

"U.S. Appl. No. 09/738,407, Notice of Allowance mailed Apr. 7, 2003", 7 pgs.

"U.S. Appl. No. 09/738,407, Response filed Mar. 13, 2003 to Final Office Action mailed Jan. 14, 2003", 10 pgs.

"U.S. Appl. No. 09/738,407, Response filed Nov. 22, 2002 to Non-Final Office Action mailed Aug. 23, 2002", 7 pgs.

"U.S. Appl. No. 09/748,791, Advisory Action mailed Aug. 4, 2004", 3 pgs.

"U.S. Appl. No. 09/748,791, Final Office Action mailed Mar. 9, 2004", 6 pgs.

"U.S. Appl. No. 09/748,791, Final Office Action mailed Aug. 23, 2005", 6 pgs.

"U.S. Appl. No. 09/748,791, Non Final Office Action mailed Feb. 21, 2003", 9 pgs.

"U.S. Appl. No. 09/748,791, Non Final Office Action mailed Sep. 17, 2003", 8 pgs.

"U.S. Appl. No. 09/748,791, Notice of Allowance mailed Sep. 20, 2006", 5 pgs.

"U.S. Appl. No. 09/748,791, Preliminary Amendment filed Feb. 21, 2001", 2 pgs.

"U.S. Appl. No. 09/748,791, Response filed May 10, 2006 to Non Final Office Action mailed Feb. 10, 2006", 8 pgs.

"U.S. Appl. No. 09/748,791, Response filed Jul. 5, 2005 to Non Final Office Action mailed Feb. 3, 2005", 7 pgs.

"U.S. Appl. No. 09/748,791, Response filed Jul. 9, 2004 to Final Office Action mailed Mar. 9, 2004", 11 pgs.

"U.S. Appl. No. 09/748,791, Response filed Jul. 21, 2003 to Non Final Office Action mailed Feb. 21, 2003", 15 pgs.

"U.S. Appl. No. 09/748,791, Response filed Nov. 23, 2005 to Final Office Action mailed Aug. 23, 2005", 7 pgs.

"U.S. Appl. No. 09/748,791, Response filed Nov. 25, 2002 to Non Final Office Action mailed Aug. 28, 2002", 7 pgs.

"U.S. Appl. No. 09/748,791, Response filed Dec. 17, 2003 to Non Final Office Action mailed Sep. 17, 2003", 10 pgs.

"U.S. Appl. No. 09/748,791, Non Final Office Action mailed Feb. 3, 2005", 6 pgs.

"U.S. Appl. No. 09/748,791, Non Final Office Action mailed Feb. 10, 2006", 9 pgs.

"U.S. Appl. No. 09/748,791, Non-Final Office Action mailed Aug. 28, 2002", 7 pgs.

"U.S. Appl. No. 09/748,791, Notice of Allowance mailed Sep. 3, 2004", 7 pgs.

"U.S. Appl. No. 10/655,569, Non-Final Office Action mailed Mar. 28, 2005", 7 pgs.

"U.S. Appl. No. 10/655,569, Notice of Allowance mailed Aug. 25, 2005", 4 pgs.

"U.S. Appl. No. 10/655,569, Response and Supplemental Preliminary Amendment filed Mar. 4, 2005 to Restriction Requirement mailed Feb. 4, 2005", 12 pgs.

"U.S. Appl. No. 10/655,569, Response filed Jul. 28, 2005 to Non-Final Office Action mailed Mar. 28, 2005", 8 pgs.

"U.S. Appl. No. 10/655,569, Restriction Requirement mailed Feb. 4, 2005", 5 pgs.

"U.S. Appl. No. 11/276,007, Preliminary Amendment filed Mar. 13, 2006", 3 pgs.

"U.S. Appl. No. 11/276,007, Response filed Oct. 20, 2008 to Non Final Office Action mailed Jun. 18, 2008", 8 pgs.

"U.S. Appl. No. 11/276,007, Notice of Allowance mailed Feb. 6, 2009", 5 pgs.

"U.S. Appl. No. 11/276,007, Non-Final Office Action mailed Jun. 18, 2008", 10 pgs.

US 6,527,714, 03/2003, Bardy (withdrawn)

* cited by examiner

EXPERT SYSTEM AND METHOD

CROSS REFERENCE TO RELATED APPLICATION(S)

This application is a continuation of U.S. patent application Ser. No. 09/748,791, filed on Dec. 26, 2000 now U.S. Pat. No. 7,181,285, the specification of which is incorporated herein by reference

TECHNICAL FIELD

The present invention relates to medical devices and in particular to a medical device programmer having an expert system to suggest therapy settings based on a patient profile.

BACKGROUND

When functioning properly, the human heart maintains its own intrinsic rhythm, and is capable of pumping adequate blood throughout the body's circulatory system. However, some people have irregular cardiac rhythms, referred to as cardiac arrhythmias. Such arrhythmias result in diminished blood circulation. One mode of treating cardiac arrhythmias uses drug therapy. Drugs are often effective at restoring normal heart rhythms. However, drug therapy is not always effective for treating arrhythmias of certain patients. For such patients, an alternative mode of treatment is needed. One such alternative mode of treatment includes the use of a cardiac rhythm management system. Such systems are often implanted in the patient and deliver therapy to the heart.

Cardiac rhythm management systems include, among other things, pacemakers, also referred to as pacers. Pacers deliver timed sequences of low energy electrical stimuli, called pace pulses, to the heart, such as via an intravascular leadwire or catheter (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly.

Cardiac rhythm management systems also include cardioverters or defibrillators that are capable of delivering higher energy electrical stimuli to the heart. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering a high energy electrical stimulus that is sometimes referred to as a defibrillation countershock. The countershock interrupts the tachyarrhythmia, allowing the heart to reestablish a normal rhythm for the efficient pumping of blood. In addition to pacers, cardiac rhythm management systems also include, among other things, pacer/defibrillators that combine the functions of pacers and defibrillators, drug delivery devices, and any other implantable or external systems or devices for diagnosing or treating cardiac arrhythmias.

One problem faced by cardiac rhythm management systems is the treatment of heart failure (also referred to as "HF"). Heart failure, which can result from long-term hypertension, is a condition in which the muscle in the walls of at least one of the right and left sides of the heart deteriorates. By way of example, suppose the muscle in the walls of the left side of the heart deteriorates. As a result, the left atrium and left ventricle become enlarged, and the heart muscle displays less contractility. This decreases cardiac output of blood through the circulatory system which, in turn, may result in an increased heart rate and less resting time between heartbeats. The heart consumes more energy and oxygen, and its condition typically worsens over a period of time.

In the above example, as the left side of the heart becomes enlarged, the intrinsic heart signals that control heart rhythm can also be impaired. Normally, such intrinsic signals originate in the sinoatrial (SA) node in the upper right atrium, traveling through and depolarizing the atrial heart tissue such that resulting contractions of the right and left atria are triggered. The intrinsic atrial heart signals are received by the atrioventricular (AV) node which, in turn, triggers a subsequent ventricular intrinsic heart signal that travels through and depolarizes the ventricular heart tissue such that resulting contractions of the right and left ventricles are triggered substantially simultaneously.

In the above example, where the left side of the heart has become enlarged due to heart failure, however, the ventricular intrinsic heart signals may travel through and depolarize the left side of the heart more slowly than in the right side of the heart. As a result, the left and right ventricles do not contract simultaneously, but rather, the left ventricle contracts after the right ventricle. This reduces the pumping efficiency of the heart. Moreover, in the case of left bundle branch block (LBBB), for example, different regions within the left ventricle may not contract together in a coordinated fashion.

Heart failure can be treated by biventricular coordination therapy that provides pacing pulses to both right and left ventricles. See, e.g., Mower U.S. Pat. No. 4,928,688. Heart failure may also result in an overly long atrioventricular (AV) delay between atrial and ventricular contractions, again reducing the pumping efficiency of the heart. Providing heart failure patients with improved pacing and coordination therapies for improving AV-delay, coordinating ventricular contractions, or otherwise increasing heart pumping efficiency continues to be area in which improved techniques and therapy protocols are needed.

SUMMARY

The present subject matter provides suggestions for, and execution of, pacing and coordination therapies for improving AV-delay, coordinating ventricular contractions, and/or otherwise increasing heart pumping efficiency of a patient's heart. In one embodiment, a medical device programmer is used to receive and/or determine a first data value of patient specific information that is used in the execution of one or more algorithms. One or more suggested pulse generator settings are calculated from the one or more algorithms based on the first data value, and the one or more suggested pulse generator settings are displayed on an interactive display screen of the medical device programmer. All or some of the one or more suggested pulse generator settings are then either programmed into the pulse generator automatically or under the direction of the physician.

The first data value derived from the patient includes any number of measurements made from one or more cardiac signals. In one embodiment, the first data value is a duration interval of one or more of a QRS complex. From the duration interval, determinations and/or suggestions are made as to one or more ventricular chambers in which to provide pacing pulses. For example, a duration interval of the QRS complex is measured from a cardiac signal and used as the first data value with the one or more algorithms. In one embodiment, the duration interval is provided by the physician as the first data value to be used with the one or more algorithms. From the one or more algorithms, a determination is made as which ventricular chamber, or both ventricular chambers to provide pacing pulses based on the duration interval of the QRS complex. In one embodiment, the determination is presented as a suggestion on a medical device programmer as to which, or both, ventricular chambers to provide pacing pulses to.

In an additional embodiment, first data value is a duration interval of an P-R interval between one or more of an atrial event and a ventricular event. From the P-R interval, a determination is made on an indicated pacing interval, $T_n$, for the AV delay based on the P-R-interval. In one embodiment, this determination of the AV delay is presented as a suggested setting on a medical device programmer for programming an implantable pulse generator. In a further embodiment, the first data value is a duration interval of a V-V-interval between a right ventricular event and a left ventricular event. From the V-V-interval, a determination is made for the pacing interval, $T_n$, for an LV offset value. In one embodiment, this determination of the LV offset is presented as a suggested setting one a medical device programmer.

Any combination of the derived pulse generator settings are then programmed into the pulse generator under the direction of the physician. In one embodiment, this is done by the physician after a review of the settings on the medical device programmer. In addition, the medical device programmer can automatically program one or more of the derived pulse generator settings with this information being made available to the physician. Any or all of the derived pulse generator settings can be changed, deleted, or used in subsequent determinations of the pulse generator settings under the direction of the physician or automatically by the algorithms of the present subject matter.

DETAILED DESCRIPTION

In the following detailed description, reference is made to the accompanying drawings that form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents.

In the following, the term "AV-Delay" is used to refer to a therapy setting "AV-Delay". In contrast, the time interval between an atrial event and a ventricular event will be referred to as a "P-R interval".

The present methods and apparatus will be described in applications involving a medical device programmer and implantable medical devices for treating heart failure including, but not limited to, implantable pulse generators such as pacemakers, cardioverter/defibrillators, pacer/defibrillators, and biventricular or other multi-site coordination devices. However, it is understood that the present methods and apparatus may be employed in unimplanted devices, including, but not limited to, external pacemakers, cardioverter/defibrillators, pacer/defibrillators, biventricular or other multi-site coordination devices, monitors and recorders.

Medical device programmers are the primary clinical tools used for changing settings, retrieving diagnostic data and conducting noninvasive tests on a patient's implantable pulse generator. These devices use inductive coils to provide bidirectional telemetry between the programmer and the implantable pulse generator. With the programmer, physicians receive and view stored cardiac and system data from the implantable pulse generator and send programming instructions back down to the implantable pulse generator.

While medical device programmers are able to display a variety of information received from the implantable pulse generator, the physician must still review and interpret the information. From this information the physician makes their decision on how best to set programmable variables of the implantable pulse generator.

Manufacturers and physicians are sensitive to the role that time-efficient programming of implantable pulse generators plays in the productivity of a pacing clinic. Given these time pressures, having programming suggestions presented to the physician would be a convenient and time saving measure. In addition, by having a list of programming suggestions the physician is better able to understand the range of options and possible therapy protocols available to best meet the patient's needs.

The present subject matter provides suggestions for therapy settings in devices for treating heart failure. Such devices can include, but are not limited to, implantable pulse generators such as pacemakers and implantable cardioverter defibrillators (ICDs). The suggested therapy settings are developed from information derived from one or more cardiac signals sensed from the patient. In one embodiment, these cardiac signals are sensed with the patient's implantable medical device. Alternatively, other means for sensing and/or recording a patient's cardiac signals are useful. Because the patient's own cardiac signal(s) are used, the suggestions for and/or programmed therapy settings are tailored to the patient.

In one embodiment, the present subject matter is implemented in a medical device programmer that receives or determines a patient's cardiac information (e.g., cardiac signal(s) sensed with their implantable pulse generator. In one embodiment, the cardiac information includes, but is not limited to, time intervals of cardiac complexes detected in the cardiac signals, along with the location of leads and electrodes within the patient's heart. This information is used to develop a patient profile. In one embodiment, the patient profile is then used to develop settings for programmable parameters within the implantable pulse generator. In one embodiment, the programmer displays the settings for consideration by the physician. Alternatively, the programmer communicates one or more of the calculated settings to the implantable pulse generator. The settings communicated to the pulse generator are then displayed on the programmer. The settings can either be accepted or be changed and programmed into the pulse generator. Alternatively, the suggested settings can be used in subsequent patient profile calculations.

Figure 1:
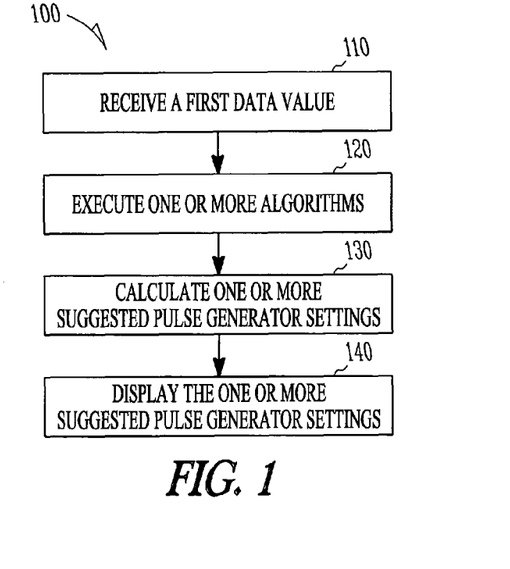
FIG. 1 is one embodiment of a method according to the present subject matter.

FIG. 1 shows one embodiment of a method 100 according to the present subject matter. At 110, a first data value is received. In one embodiment, the first data value is patient specific information derived from one or more cardiac signals sensed from the patient. Patient specific information can include, but is not limited to, a duration interval of one or more of a QRS complex, and/or a duration interval of one or more P-R intervals, a duration interval of a V-V-interval, where any of duration intervals can be determined from one representative interval, or an average or mean value of intervals. In addition, the first data value is determined automatically from sensed or recorded cardiac signals. Alternatively, the first data value is determined from manual measurements made on scaled images of the cardiac signals.

At 120, one or more algorithms are executed, where the one or more algorithms use the first data value. In one embodiment, the one or more algorithms are executed within a medical device programmer. The one or more algorithms, however, could be executed in a device having the ability to receive the first data value and the ability to execute the one or more algorithms. At 130, one or more suggested pulse generator settings are calculated with the one or more algorithms based on the first data value. The present subject matter is, however, not limited to using only the first data value in determining the suggested pulse generator settings. Additional data and/or patient information might also be used in, or in conjunction with, the one or more algorithms in determining the pulse generator settings. The one or more suggested pulse generator settings are displayed at 140. In one embodiment, the suggested pulse generator settings are displayed on an interactive display screen. In one embodiment, the interactive display screen is part of the medical device programmer.

In addition to using the first data value to determine the one or more suggested pulse generator settings, the present subject matter allows for two or more determinations of the one or more suggested pulse generator settings to be made. From the two or more determinations, a single set of the one or more suggested pulse generator settings can be derived. For example, an average of the one or more suggested pulse generator settings can be determined for N samples. The averaged suggested settings are then displayed.

Figure 2:
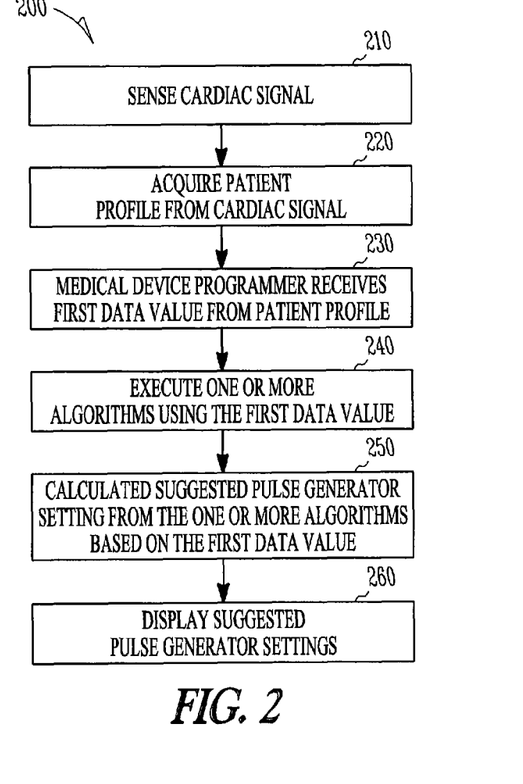
FIG. 2 is one embodiment of a method according to the present subject matter.

FIG. 2 shows an additional embodiment of a method 200 according to the present subject matter. The method 200 generally proceeds through three stages, where each of the stages is performed sequentially, and each stage is completed prior to a subsequent stage being started. It is recognized, however, that the present subject matter need not proceed through set stages, where the procedure used in present subject matter can be performed at least partially or completely simultaneously after receiving all necessary information to perform the algorithms.

At 210, a cardiac signal is sensed from a patient's heart. In one embodiment, the cardiac signal is electronically sensed, where the signal is a far-field signal sensed in a variety of ways. For example, the cardiac signal is sensed through the use of a surface 12-lead ECG measurement. Alternatively, the cardiac signal is sensed through the use of a programmer recorded monitor (PRM) surface ECG system.

At 220, a patient profile is acquired from the cardiac signal. In one embodiment, the patient profile includes a first data value derived from the sensed cardiac signal. For example, the first data value is a duration interval of one or more QRS complexes detected in the patient's sensed cardiac signal. Alternatively, the first data value is a P-R interval value or a V-V-interval value between a left and right ventricular contraction. Alternatively, a previous patient profile could be updated by the medical device programmer with the first data value, where data values from one or more patient profiles are used in determining a final data value to be used in the algorithms.

The medical device programmer then receives the first data value at 230. In one embodiment, the first data value is provided to the medical device programmer. Alternatively, the medical device programmer determines the first data value. Once the medical device programmer receives the first data value at 130, the electronic control circuitry within the programmer executes one or more algorithms at 140, where the one or more algorithms use the first data value. In one embodiment, the electronic control circuitry within the programmer is controlled by the user to execute the one or more algorithms. Alternatively, the electronic control circuitry executes the one or more algorithms automatically once the first data value is received.

At 250, the electronic control circuitry calculates suggested pulse generator settings from the one or more algorithms using the first data value. Suggested pulse generator settings are displayed on a display screen at 260. In one embodiment, the suggested pulse generator settings are, in addition to being displayed on the display screen, also programmed into the pulse generator. The user then reviews the programmed information. Based on the review, the user can then accept the programmed values. Alternatively, the user can change one or more of the values. In addition, the user could also request the values be recalculated using a newly derived first data value, or recalculated using a first data value derived from the first data value used in determining the pulse generator settings and a newly derived first data value, or a default first data value for the patient. The user views the suggested pulse generator settings and decides to accept some or all the suggested values, change some or all the suggested values and to program, not program or change the programmed the suggested values into the implantable medical device.

In one example, the implantable pulse generator includes pacemaker functions, where the pacemaker functions could be operating in any number of implantable or external rhythm management devices (e.g., ICDs and/or pacemakers, implantable or external). Suggested pulse generator settings for the pacemaker function include, but are not limited to, which of either or both ventricular chambers to pace, a time interval for an AV-delay (the length of time between an atrial sensed or atrial paced event and the delivery of a ventricular output pulse, unless shortened by a sensed intrinsic ventricular event prior to the AV interval timing out) and/or a time interval for an LV offset (the length of time between a sensed or paced event in a first ventricle and the delivery of an output pulse to a second ventricle). Deriving these suggested pulse generator settings will be more fully elaborated on below.

Figure 3:
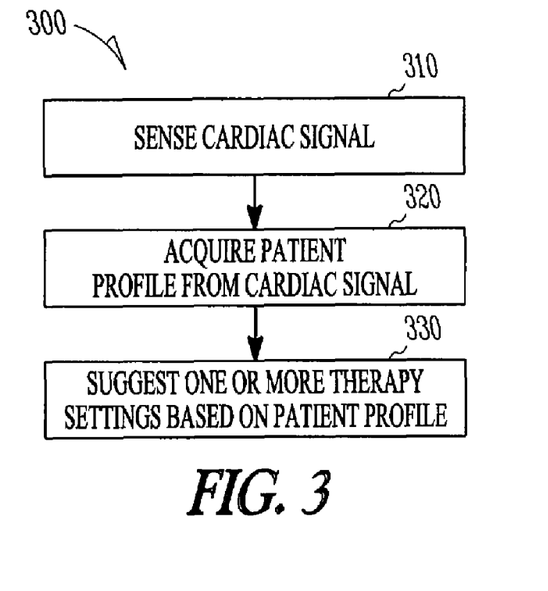
FIG. 3 is one embodiment of a method according to the present subject matter.

FIG. 3 shows an additional embodiment of a method 300 according to the present subject matter. At 310, a cardiac signal that includes QRS complexes is sensed from a patient's heart through the use of a surface 12-lead ECG measurement or a PRM surface ECG system. At 320, a patient profile is acquired from the sensed cardiac signal. In one embodiment, the patient profile includes the first data value as previously described. In the present embodiment, the first data value is a duration interval of one or more QRS complexes detected in the patient's sensed cardiac signal. Measuring the duration interval of QRS complexes is accomplished in any number of ways. For example, the duration interval of the QRS complex is measured manually. In one embodiment, manually measuring the QRS complex duration interval is accomplished by sensing the cardiac signal using either of the above-mentioned techniques and recording/printing the sensed cardiac signal on a paper strip chart recording at 50 millimeters/second. In one embodiment, the QRS complex duration intervals are measured from cardiac signals sensed on leads II, $V_1$ and $V_6$ of a 12-lead ECG, where lead $V_6$ is placed at the midaxillary line, at the same level as lead $V_4$. In one embodiment, the QRS duration is measured from the printout of the cardiac signal using standard practice for determining the start and end of the QRS complex. For example, the QRS duration is measured between a point at which the initial deflection for the Q-wave is sensed and a point where the S-wave returns to baseline of the cardiac signal.

Alternatively, the duration of the QRS complex is measured automatically by an external surface ECG machine. For example, QRS complex duration intervals are measured from cardiac signals sensed from leads II and $V_1$ of a PRM surface ECG system, where lead $V_1$ is placed at the fourth intercostal space, just to the right of the sternum.

At 330, the duration interval of the QRS complex is received by the medical device programmer as the first data value for use with the one or more algorithms, where the one or more algorithms provide suggestions for therapy settings for an implantable pulse generator. In one example, the implantable pulse generator includes pacemaker functions, where the pacemaker functions could be operating in any number of implantable or external rhythm management devices (e.g., ICDs and/or pacemakers, implantable or external). Therapy settings suggested for the pacemaker function include, but are not limited to, which of either or both ventricular chambers to pace, a time interval for an AV-delay (the length of time between an atrial sensed or atrial paced event and the delivery of a ventricular output pulse, unless shortened by a sensed intrinsic ventricular event prior to the AV interval timing out) and/or a time interval for an LV offset (the length of time between a sensed or paced event in a first ventricle and the delivery of an output pulse to a second ventricle).

Examples where suggested therapy settings would be useful include pulse generators that deliver pacing pulses to multiple ventricular or atrial sites, including so-called biventricular pacemakers where pacing pulses are delivered to both ventricles by separate electrodes during a cardiac cycle. (See, e.g., U.S. Pat. Nos. 5,792,203 and 4,928,688, referred to herein as the '203 and '688 patents, which are hereby incorporated by reference.) Biventricular pulse generators have been found to be useful in treating heart failure (HF), a clinical syndrome in which an abnormality of cardiac function causes cardiac output to fall below a level adequate to meet the metabolic demand of peripheral tissues. HF can be due to a variety of etiologies, with ischemic heart disease being the most common. Some HF patients suffer from some degree of AV block such that their cardiac output can be improved by synchronizing atrial and ventricular contractions with dual-chamber pacing using a short programmed AV delay time. It has also been shown, however, that some HF patients suffer from intraventricular conduction defects (a.k.a. bundle branch blocks). The cardiac outputs of these can be increased by improving the synchronization of right and left ventricular contractions with biventricular pacing. The present subject matter provides suggested programmable parameter values for treating these cardiac conditions.

Ventricular Chamber

In one embodiment, the suggestion for which ventricular chamber to pace (left, right or both) is based on the sensed cardiac conduction between the right and left ventricles of the heart. Different timing relationships between cardiac complexes in the cardiac signals sensed from the right and left ventricular regions can indicate different conduction disorder types. For example, in bundle branch block type disorders regions of the left or right ventricle do not contract together in a coordinated fashion. As a result, the left and right ventricles do not contract simultaneously, but rather, the left ventricle contracts after the right ventricle or vice versa. As a result, the pumping efficiency of the heart is reduced. To increase the pumping efficiency of the heart, identifying and selecting a ventricular pacing location, or locations, that allow for synchronized ventricular contractions would be beneficial to patients with conduction disorder problems.

Figure 4:
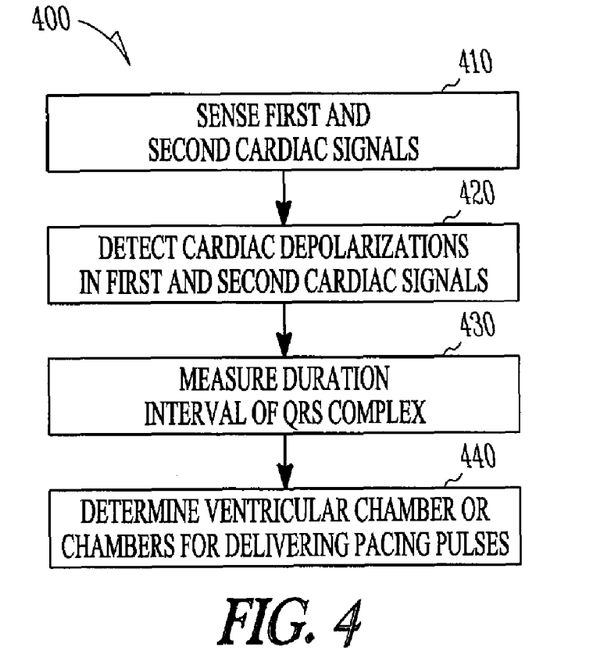
FIG. 4 is one embodiment of a method according to the present subject matter.

Referring to FIG. 4, there is shown one embodiment of a method 400 for selecting a ventricular stimulation chamber for resynchronization therapy. At 410, a first cardiac signal is sensed from a right ventricular region and a second cardiac signal is sensed from a left ventricular region. In one embodiment, the first cardiac signal is sensed from an apex of the right ventricular, while the second cardiac signal is sensed from a left ventricular free wall. Alternatively, the first cardiac signal is sensed from any number of positions within the right ventricle and/or the second cardiac signal is sensed from an endocardial or transvenous location (i.e., lead implanted in coronary vein with electrode adjacent LV). Other locations for sensing these signals are also possible. At 420, cardiac depolarizations are detected in each of the first and second cardiac signals. In one embodiment, the cardiac depolarizations include R-waves, which are indications of ventricular contractions. The time at which the ventricular contractions occurred is then recorded, where $R_L$ is designated as the time at which the depolarization in the left ventricle occurred and $R_R$ is designated as the time at which the depolarization in the right ventricle occurred. In one embodiment, the time the R-wave occurred is taken as the peak (i.e., the point of maximum deflection during depolarization) of the R-wave.

At 430, the duration interval of the QRS complexes in the sensed cardiac signals are measured. As previously discussed, measuring the duration interval of QRS complexes is accomplished in any number of ways. For example, the duration interval of the QRS complex is measured manually from a paper strip chart of the patient's sensed cardiac signals or automatically by an external surface ECG machine. At 440, the stimulation chamber, or chambers, are then determined based upon the duration interval of the QRS complexes and the time of occurrence for $R_L$ and $R_R$.

In one embodiment, the determination as to the ventricular chamber or chambers to pace is based on the comparison of the duration interval of the QRS complexes to an established value and the value of the difference between $R_L$ and $R_R$. For example, when the duration interval of the QRS complexes is greater than or equal to 120 milliseconds and the difference between $R_L$ and $R_R$ (i.e., $R_L-R_R$) is greater than 0 (zero), then the patient is likely a left bundle branch block type. In this situation the recommended pacing chamber would be either the left ventricle or biventricular (left ventricle and right ventricle). Alternatively, when the duration interval of the QRS complexes is greater than or equal to 120 milliseconds and the difference between $R_L$ and $R_R$ (i.e., $R_L-R_R$) is less than or equal to 0 (zero), then the patient is likely a right bundle branch block type. In this situation the recommended pacing chamber would be the right ventricle.

AV Delay Interval

The system and method of the present subject matter also allows for an AV delay interval to be computed from information derived from sensed cardiac signals. One example of computing an AV delay is described in U.S. patent application "System Providing Ventricular Pacing and Biventricular Coordination" commonly assigned Ser. No. 09/316,588, which is hereby incorporated by reference. The suggested AV delay is then displayed as a suggested programmable value for the implantable pulse generator, which in this instance would be a dual chamber implantable pulse generator. In one embodiment, the AV delay is computed based at least in part on an underlying intrinsic P-R interval. When programmed into the implantable pulse generator the AV delay is used to time the delivery of coordinated atrial/ventricular pacing therapy when atrial heart rhythms are not arrhythmic.

In one embodiment, the system obtains P-R intervals between atrial events and successive ventricular events. In one embodiment, the intervals are calculated based on the sensed P-waves and R-waves. The system computes an AV delay interval based at least on a most recent P-R interval duration and a previous value of the P-R interval. The system can then be used to program the implantable pulse generator to deliver coordinated atrial pacing and ventricular pacing pulses with the AV delay interval.

Figure 5:
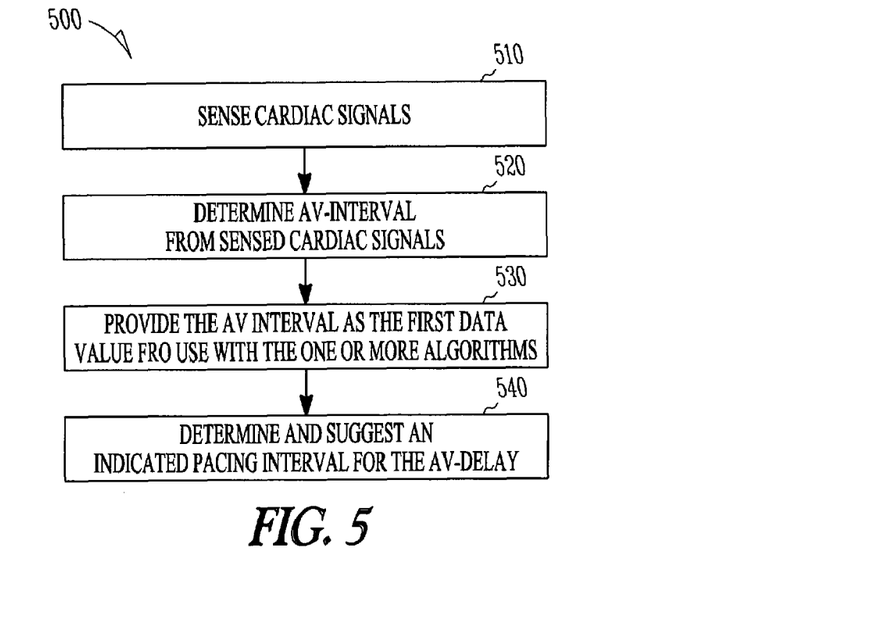
FIG. 5 is one embodiment of a method according to the present subject matter.

Referring to FIG. 5, there is shown one embodiment of a method 500 for computing the AV delay interval. At 510, cardiac signals are sensed from the heart. In one embodiment, an atrial cardiac signal is sensed from an atrial location and a ventricular cardiac signal is sensed from a ventricular location. Paced or sensed atrial events are detected in the atrial signal, and paced or sensed ventricular events are detected in the ventricular signal. At 520, a duration of a P-R interval is measured from a sensed atrial event and a subsequently sensed ventricular event.

The measured P-R interval is then provided as the first data value for use with the one or more algorithms at 530. The one or more algorithms then use the measured P-R interval to determine and suggest an indicated pacing interval, $T_n$, for the AV delay at 440. In one example, the indicated pacing interval, $T_n$, for the AV delay is described by $T_n = a \cdot w \cdot AV_n + (1-w) \cdot T_{n-1}$, when $AV_n$ is concluded by an intrinsic ventricular beat, otherwise is described by $T_n = b \cdot w \cdot AV_n + (1-w) \cdot T_{n-1}$ when $AV_n$ is concluded by a paced ventricular beat, where $T_{n-1}$ is the previous value of the indicated P-R interval, $AV_n$ is the time interval corresponding to the most recent P-R interval, and a, b, and w are coefficients. In one embodiment, weighting coefficient w, intrinsic coefficient a, and paced coefficient b, are variables. Different selections of w, a, and b, will result in different operation of the present method and apparatus. For example, as w increases the weighting effect of the most recent P-R interval ($AV_n$) increases and the weighting effect of the previous first indicated pacing interval $T_{n-1}$ decreases.

In one embodiment, w is equal to 1/16 (0.0625). In another embodiment, w is equal to 1/32. Another possible range for w is from w equal to 1/2 to w equal to 1/1024. A further possible range for w is from w approximately equal to 0 to w approximately equal to 1. Other values of w, which need not include division by powers of two, may be substituted without departing from the present method and apparatus.

In one embodiment, intrinsic coefficient a, is selected to be less than (or, alternatively, less than or equal to) 1.0. In one example, the intrinsic coefficient a is selected to be lesser in value than the pacing coefficient b. In one embodiment, a is approximately 0.6 and b is approximately 1.5. In another embodiment, a=1.0 and b=1.05. One possible range for a is from a=0.6 to a=1.0, and for b is from b=1.05 to b=1.5. The coefficients may vary without departing from the present method and apparatus.

In one embodiment, these coefficients are entered into the programmer by the user. In another embodiment, the user selects a desired performance parameter (e.g., desired degree pacing vs. sensing, desired attack slope, desired decay slope, etc.) from a corresponding range of possible values, and the programmer automatically selects the appropriate combination of coefficients to provide a filter setting that corresponds to the selected user-programmed performance parameter, as illustrated generally by Table 1. Other levels of programmability or different combinations of coefficients may also be used.

TABLE 1

Example of Automatic Selection of Aspects of Filter Setting Based on a User-Programmable Performance Parameter, Such as for AV Delay Regulation

| User-Programmable Performance Parameter | Intrinsic Coefficient a | Paced Coefficient b |
|---|---|---|
| 1 (Less Aggressive Attack/Decay) | 1.0 | 1.05 |
| 2 | 0.9 | 1.2 |
| 3 | 0.8 | 1.3 |
| 4 | 0.7 | 1.4 |
| 5 (More Aggressive Attack/Decay) | 0.6 | 1.5 |

In a further embodiment, the implantable device uses a mapping, such as illustrated in Table 1, in a feedback control loop to automatically select the "performance parameter" and corresponding coefficients. The user programs a mean sense frequency goal. The implantable pulse generator measures the mean frequency of sensed ventricular events ("measured mean sense frequency") over a predetermined interval of time or predetermined number of A-V intervals, and adjusts the performance parameter and corresponding coefficients to direct the measured mean sense frequency toward the mean sense frequency goal.

LV Offset

In addition to providing suggested AV-delay values, the present subject matter also provides a suggested LV offset value to be used in a cardiac rhythm management system having biventricular pacing. The suggested LV offset value provides a time interval for pacing pulses to coordinate the left and right ventricles for more efficient pumping. The system and method of the present subject matter compute an LV offset interval from information derived from sensed ventricular cardiac signals. Once the suggested LV offset interval is determined, the value is displayed and can subsequently be programmed into the implantable pulse generator having the biventricular pacing capability. In one embodiment, the LV offset interval is computed based at least in part on an underlying intrinsic V-V interval and a previously stored value of a first indicated pacing interval.

Figure 6:
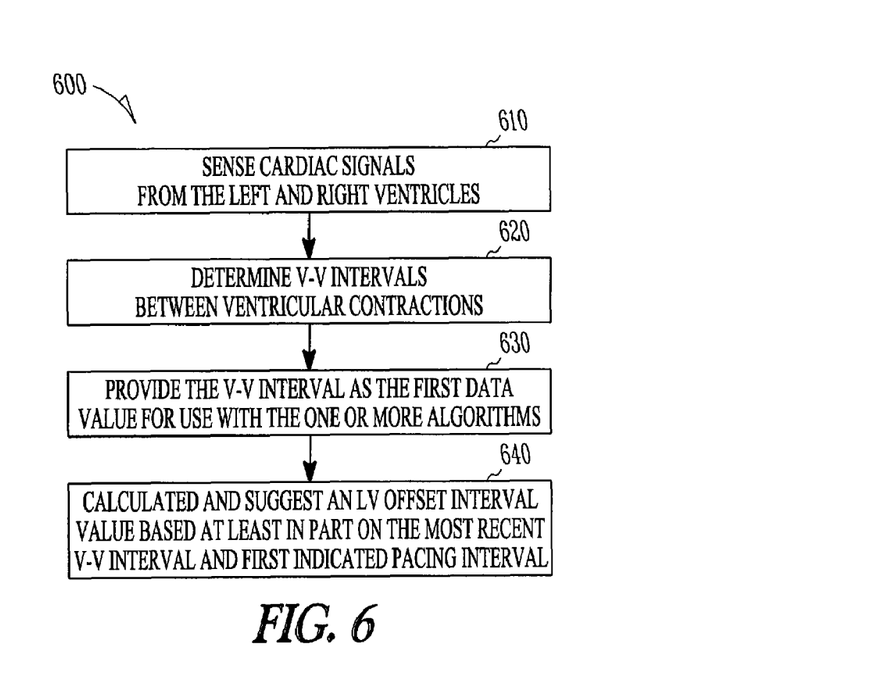
FIG. 6 is one embodiment of a method according to the present subject matter.

Referring to FIG. 6, there is shown one embodiment of a method 600 for computing the LV offset interval. At 610, cardiac signals are sensed from the heart. In one embodiment, a right ventricular cardiac signal is sensed from a right ventricular location and a left ventricular cardiac signal is sensed from a left ventricular location. From the right and left ventricular cardiac signals, the duration interval of V-V intervals between successive sensed or evoked ventricular contractions are measured at 620. These V-V intervals are referred to as the most recent V-V interval ($VV_n$).

The measured V-V interval is then provided as the first data value for use with the one or more algorithms at 630. Based in part on the duration of the most recent V-V interval and a first indicated pacing interval $T_{n-1}$ the LV offset interval is calculated and suggested at 640. In one embodiment, computing the LV offset is accomplished by using the value of the most recent V-V interval, $VV_n$, and the previous value of the first indicated pacing interval $T_{n-1}$. These values are each scaled by respective constants a, w and b, and then summed to obtain a new value of the first indicated pacing interval ($T_n$). In one embodiment, the coefficients a, w and b are different values, and are either programmable, variable, or constant.

If no ventricular beat is sensed during the new first indicated pacing interval, $T_n$, which is measured as the time from the occurrence of the ventricular beat concluding the most recent V-V interval $VV_n$, a ventricular pacing pulse is delivered upon the expiration of the new first indicated pacing interval $T_n$. In one embodiment, the new first indicated pacing interval $T_n$ is described by $T_n = a \cdot w \cdot VV_n + (1-w) \cdot T_{n-1}$, if $VV_n$ is concluded by an intrinsic beat, where a is an intrinsic coefficient, otherwise $T_n$ is described by $T_n = b \cdot w \cdot VV_n + (1-w) \cdot T_{n-1}$ if $VV_n$ is concluded by a paced beat, where b is a paced coefficient. In both equations, w is a weighting coefficient, $VV_n$ is the most recent V-V interval duration, and $T_{n-1}$ is the previous value of the first indicated pacing interval. If no ventricular beat is sensed during the new first indicated pacing interval $T_n$, which is measured as the time from the occurrence of the ventricular beat concluding the most recent V-V interval $VV_n$, then a ventricular pacing pulse is delivered upon the expiration of the new first indicated pacing interval $T_n$.

The above-described parameters (e.g., a, b, w) are stated in terms of time intervals (e.g., $VV_n$, $T_n$, $T_{n-1}$). However, an alternate system may produce results in terms of rate, rather than time intervals, without departing from the present method and apparatus. In one embodiment, weighting coefficient w, intrinsic coefficient a, and paced coefficient b, are variables. Different selections of w, a, and b, will result in different operation of the present method and apparatus. For example, as w increases the weighting effect of the most recent V-V interval $VV_n$ increases and the weighting effect of the previous first indicated pacing rate $T_{n-1}$ decreases. In one embodiment, w is equal to 1/16 (0.0625). In another embodiment, w is equal to 1/32. Another possible range for w is from w equal to 1/2 to w equal to 1/1024. A further possible range for w is from w approximately equal to 0 to w being approximately equal to 1. Other values of w, which need not include division by powers of two, may be substituted without departing from the present method and apparatus.

In one embodiment, intrinsic coefficient a, is selected to be greater than 0.5, or to be greater than 1.0. In one example, the intrinsic coefficient a is selected to be lesser in value than the pacing coefficient b. In one example, a is approximately equal to 1.1 and b is approximately equal to 1.2. In another embodiment a=0.9 and b=1.1. One possible range for a is from a=0.5 to a=2.0, and for b is from b=1.0 to b=3.0. The coefficients may vary without departing from the present method and apparatus.

In one example of determining an LV offset value, ventricular depolarizations are detected in the sensed ventricular cardiac signals. V-V intervals are recorded between successive ventricular depolarizations. In a first embodiment, the V-V interval is initiated by a right ventricular beat (paced or sensed), and the V-V interval is then concluded by the next right ventricular beat (paced or sensed). In a second embodiment, the V-V interval is initiated by a left ventricular beat (paced or sensed), and the V-V interval is then concluded by the next left ventricular beat (paced or sensed). In a third embodiment, the V-V interval is initiated by either a right or left ventricular beat, and the V-V interval is then concluded by the next right or left ventricular beat that occurs after expiration of a refractory period of approximately between 130 milliseconds and 500 milliseconds (e.g., 150 milliseconds). Left or right ventricular beats occurring during the refractory period are ignored. Using the refractory period ensures that the beat concluding the V-V interval is associated with a subsequent ventricular contraction, rather than a depolarization associated with the same ventricular contraction, in which the depolarization is merely sensed in the opposite ventricle from the initiating beat. Such a refractory period can also be used in conjunction with the first embodiment (V-V interval initiated and concluded by right ventricular beats) or the second embodiment (V-V interval initiated and concluded by left ventricular beats).

Based on the measured V-V interval the first indicated pacing interval ($T_n$) (i.e., an LV offset) is computed. The first indicated pacing interval is then displayed as a suggested value to be programmed for biventricular pacing. Once programmed into the implantable pulse generator, the first indicated pacing interval is used to coordinate the contractions of the right and left ventricles so as to provide more efficient pumping of blood by the heart.

In one embodiment, the coefficients a, b, w are programmable by the user in order to obtain a desired degree of pacing vs. sensing. In another embodiment, the user selects a desired performance parameter (e.g., desired degree of pacing vs. sensing, etc.) from a corresponding range of possible values, and programmer automatically selects the appropriate combination of coefficients to provide a filter setting that corresponds to the selected user-programmed performance parameter, as illustrated generally by Table 2. Other levels of programmability or different combinations of coefficients may also be used.

TABLE 2

Example of Automatic Selection of Aspects of Filter Setting Based on a User-Programmable Performance Parameter Such as For Providing Biventricular Coordination Therapy.

| User-Programmable Performance Parameter | Intrinsic Coefficient a | Paced Coefficient b |
|---|---|---|
| 1 (More Pacing) | 0.6 | 1.05 |
| 2 | 0.7 | 1.2 |
| 3 | 0.8 | 1.3 |
| 4 | 0.9 | 1.4 |
| 5 (Less Pacing) | 1.0 | 1.5 |

In a further embodiment, a mapping is used, such as illustrated in Table 2, in a feedback control loop to automatically select the "performance parameter" of Table 2 and corresponding coefficients. The user programs a mean pacing frequency goal. The mean pacing frequency is measured over a predetermined interval of time or predetermined number of V-V intervals. The measured mean pacing is compared to the mean pacing frequency goal. If the measured mean pacing frequency is higher than the goal mean pacing frequency, the performance parameter in Table 2 is incremented/decremented toward less pacing. Conversely, if the measured mean pacing frequency is lower than the goal mean pacing frequency, the performance parameter in Table 2 is incremented/decremented toward more pacing. In a further embodiment, the measured mean pacing frequency is compared to values that are slightly offset about the goal mean pacing frequency (e.g., goal mean pacing frequency+/−Δ) to provide a band of acceptable measured mean pacing frequencies within which the performance parameter is not switched.

Programmer

Figure 7:
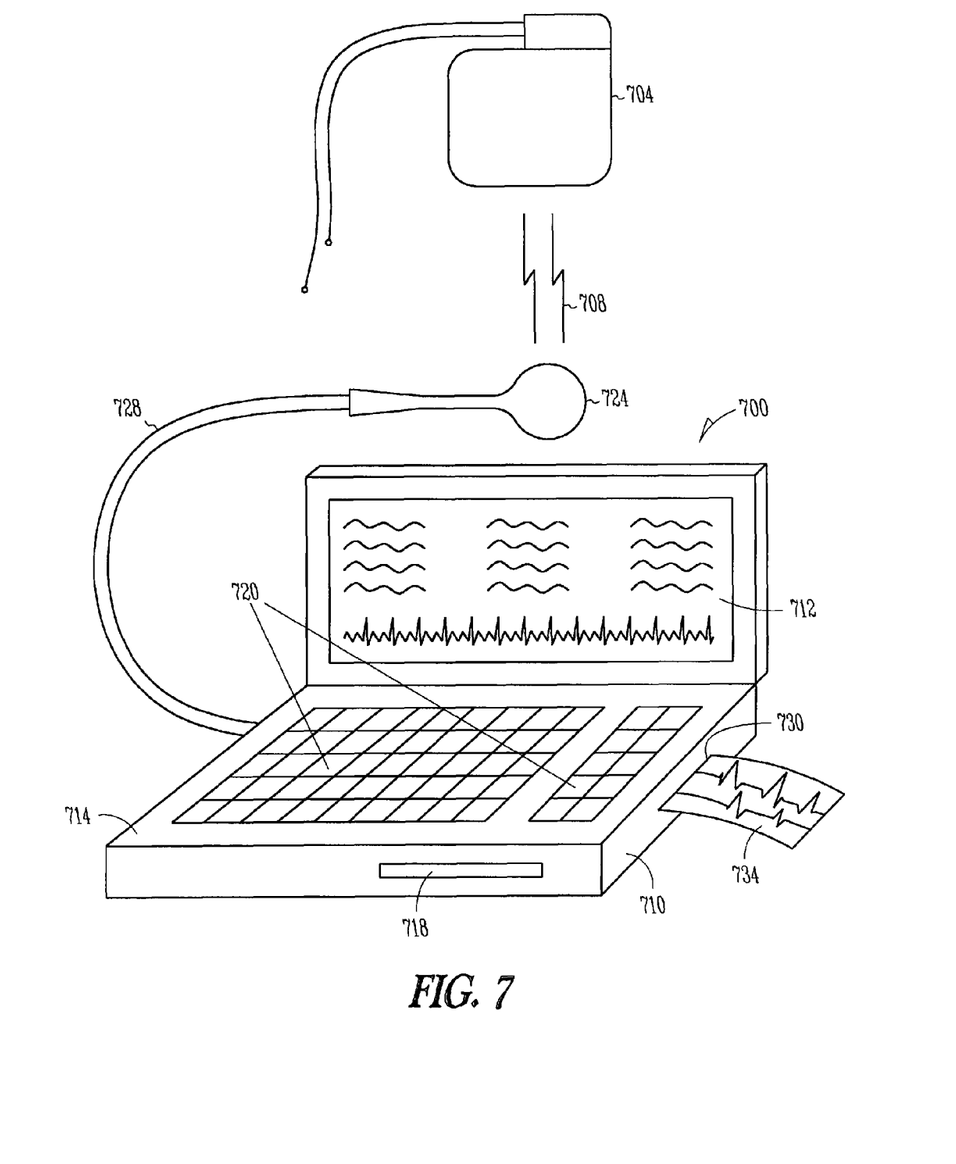
FIG. 7 is a perspective of a medical device programmer and an implantable medical device with leads according to one embodiment of the present subject matter.

FIG. 7 shows one embodiment of a medical device programmer 700 according to the present subject matter. The medical device programmer 700 is adapted to be positioned outside the human body for communication with an implantable medical device 704. In one embodiment, a communication link 708 is established between the medical device programmer 700 and the implantable medical device 704. In one embodiment, the communication link 708 is a radio frequency link.

In one embodiment, the medical device programmer 700 includes electronic circuitry within a housing 710, where a graphics display screen 712 is disposed on an upper surface 714 of the housing 710. The programmer 700 further includes a drive 718 for reading and writing instructions used by the electronic circuitry of the programmer 700. The graphics display screen 712 is operatively coupled to the electronic circuitry within the housing 710 and is adapted to provide a visual display of graphics and/or data to the user.

The programmer 700 further includes input devices to the electronic circuitry. For example, the programmer 700 includes a touch-sensitive display screen, such that the user interacts with the electronic circuitry by touching identified regions of the screen with either their finger or with a stylus (not shown). In addition, the programmer 700 further includes an alphanumeric key board 720 for providing information, such as programmable values for the implantable medical device 704, to the electronic circuitry and the medical device 704.

The programmer 700 further includes a programming head 724. The programming head 724 is used to establish the communication link 708 between the electronic circuitry within the programmer 700 and the implantable medical device 704. The telemetry link between the implantable medical device 704 and the programmer 700 allows the electronic circuitry coupled to the graphics display screen 712 to be coupled to the electronic control circuitry of the implantable medical device 704. The programming head 724 is coupled to the electronic circuitry of the medical device programmer through cable 728. FIG. 7 also shows the programmer 700 having a printer 730 which allows for cardiac signals received from the implantable medical device 704 and displayed on the graphics display screen 712 to be displayed on a paper printout 734. Adjustments for printer speed and scale of the printed cardiac signals is adjustable through the use of the display screen 712 and the electronic circuitry within the programmer 700.

Figure 8:
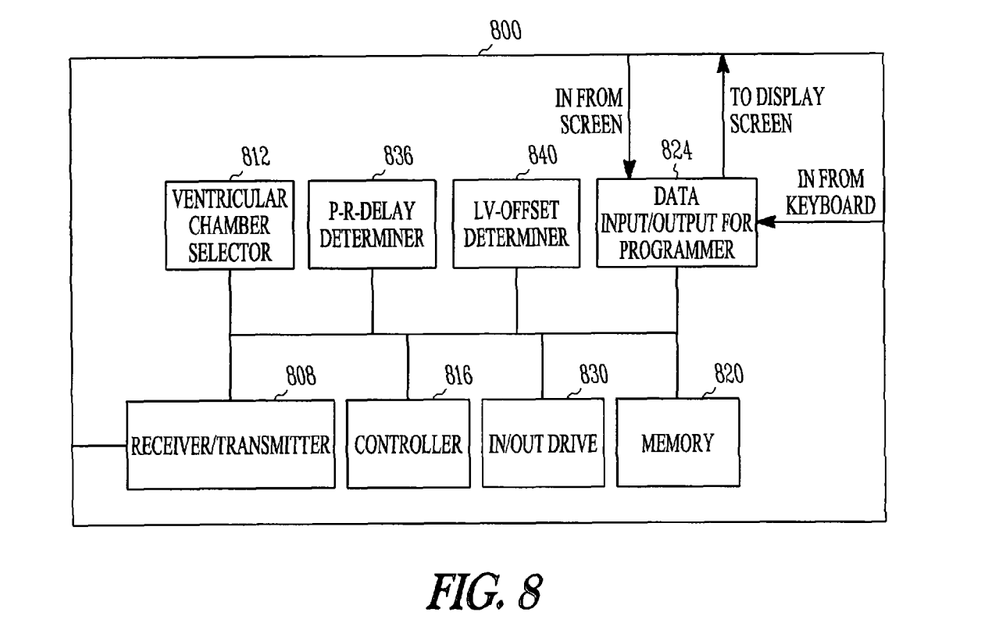
FIG. 8 is a block diagram of a medical device programmer according to one embodiment of the present subject matter.

FIG. 8 shows one embodiment of control circuitry 800 for the programmer 700. The control circuitry 800 includes a receiver/transmitter circuit 808, a ventricular chamber selector 812, a controller 816, a memory 820, a data input/output 824, an in/out drive 830, a P-R delay determiner 836 and an LV-offset determiner 840. These components are inner connected and communicate via bus 844.

In one embodiment, the control circuitry receives a first data input, as previously described, through the data input 824. The control circuitry 800 then executes one or more algorithms, as previously described, that use the first data value and calculates one or more suggested pulse generator settings from the one or more algorithms based on the first data value. The suggested pulse generator settings are then displayed on the display screen (not shown in FIG. 8) for review by the user.

As previously discussed, the first data input can be used to suggest one or more ventricular chambers in which to provide pacing pulses. For this embodiment, the first data value is the duration interval of a QRS complex. In one embodiment, the receiver/transmitter 808 receives intrinsic intracardia electrograms recorded from the left and right ventricle, as previously discussed. The ventricular chamber selector 812 then determines the difference between $R_L$ and $R_R$, where $R_L$ is the time at which the depolarization in the left ventricle occurred and $R_R$ is the time at which the depolarization in the right ventricle occurred. The ventricular chamber selector 812 then suggests one or more ventricular chambers in which to provide pacing pulses based on the duration interval of the QRS complex and the difference between $R_L$ and $R_R$, as previously described.

The first data input can also be used by the control circuitry 800 to suggest a pacing interval, $T_n$, for an AV delay based on the P-R interval. For this embodiment, the receiver/transmitter 808 receives an atrial cardiac signal having atrial events and a ventricular cardiac signal having ventricular events, as previously described. The P-R delay determiner 836 then measures the duration interval of the P-R interval between an atrial event and a ventricular event, and provides the P-R interval as the first data value for use with the one or more algorithms. The P-R delay determiner 836 then suggests an indicated pacing interval, $T_n$, for an AV delay based on the P-R interval, as previously described.

The first data input can also be used by the control circuitry 800 to suggest a pacing interval, $T_n$ for an LV offset based on the V-V interval. For this embodiment, the receiver/transmitter 808 receives a right ventricular cardiac signal having ventricular events and a left ventricular cardiac signal having ventricular events, as previously described. The LV-offset determiner 840 then measures the duration interval of the V-V interval between a right ventricular event and a left ventricular event, and provides the V-V-interval as the first data value for use with the one or more algorithms. The LV-offset determiner 840 then suggests an LV offset value based on the V-V-interval, as previously described.

Figure 9A:
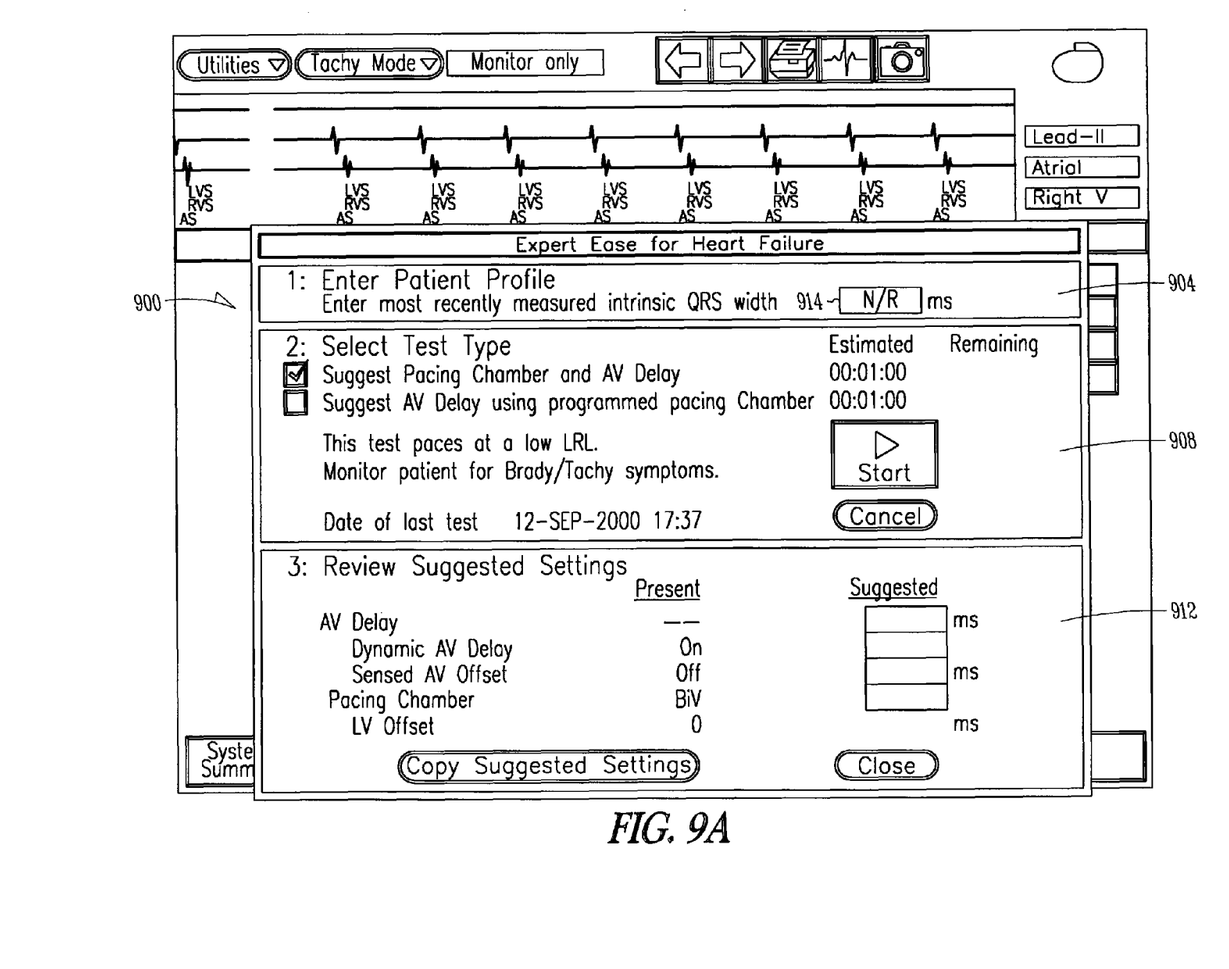
FIG. 9A is a schematic view of an interactive display screen of a medical device programmer according to one embodiment of the present subject matter.
Figure 9B:
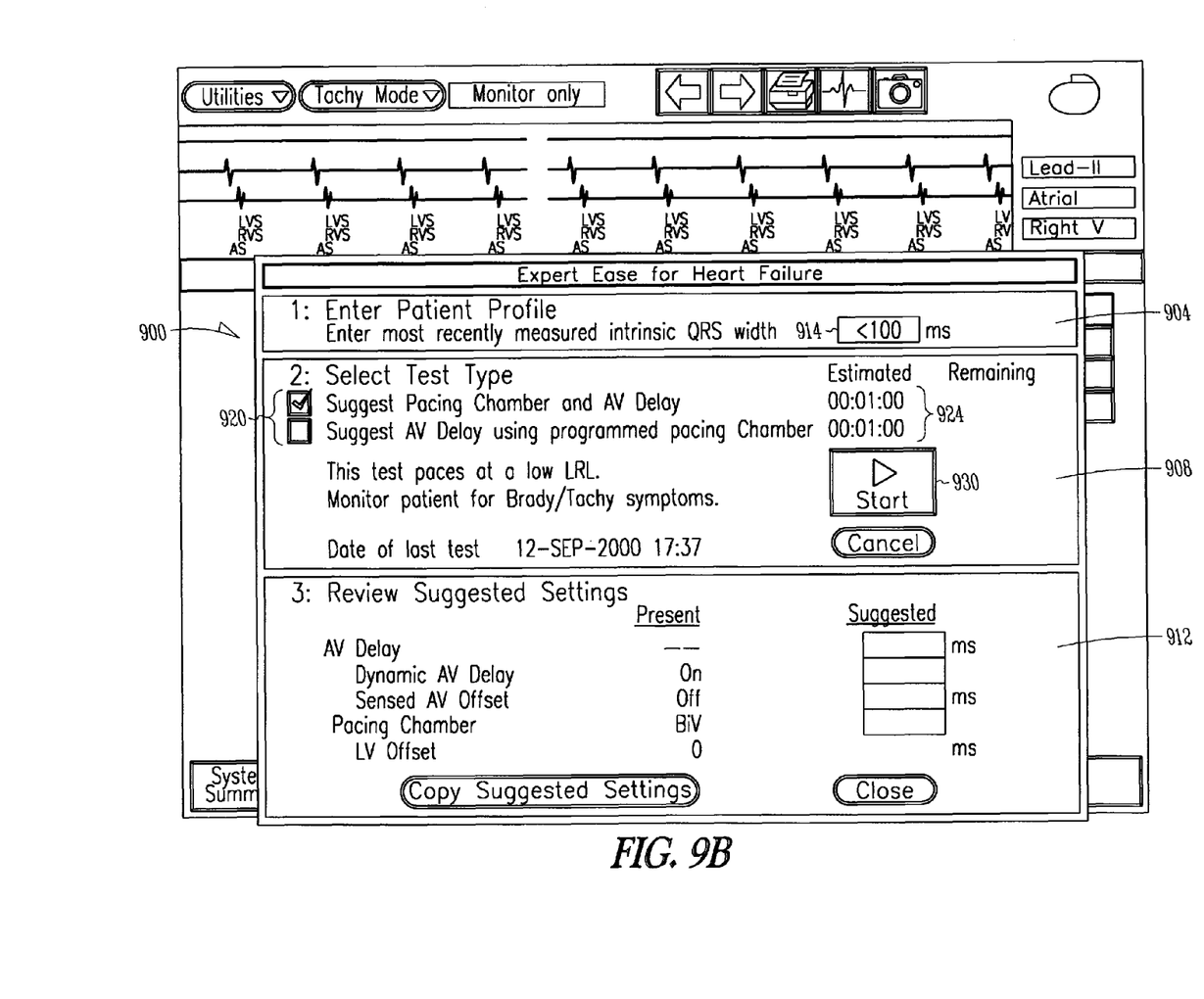
FIG. 9B is a schematic view of an interactive display screen of a medical device programmer according to one embodiment of the present subject matter.
Figure 9C:
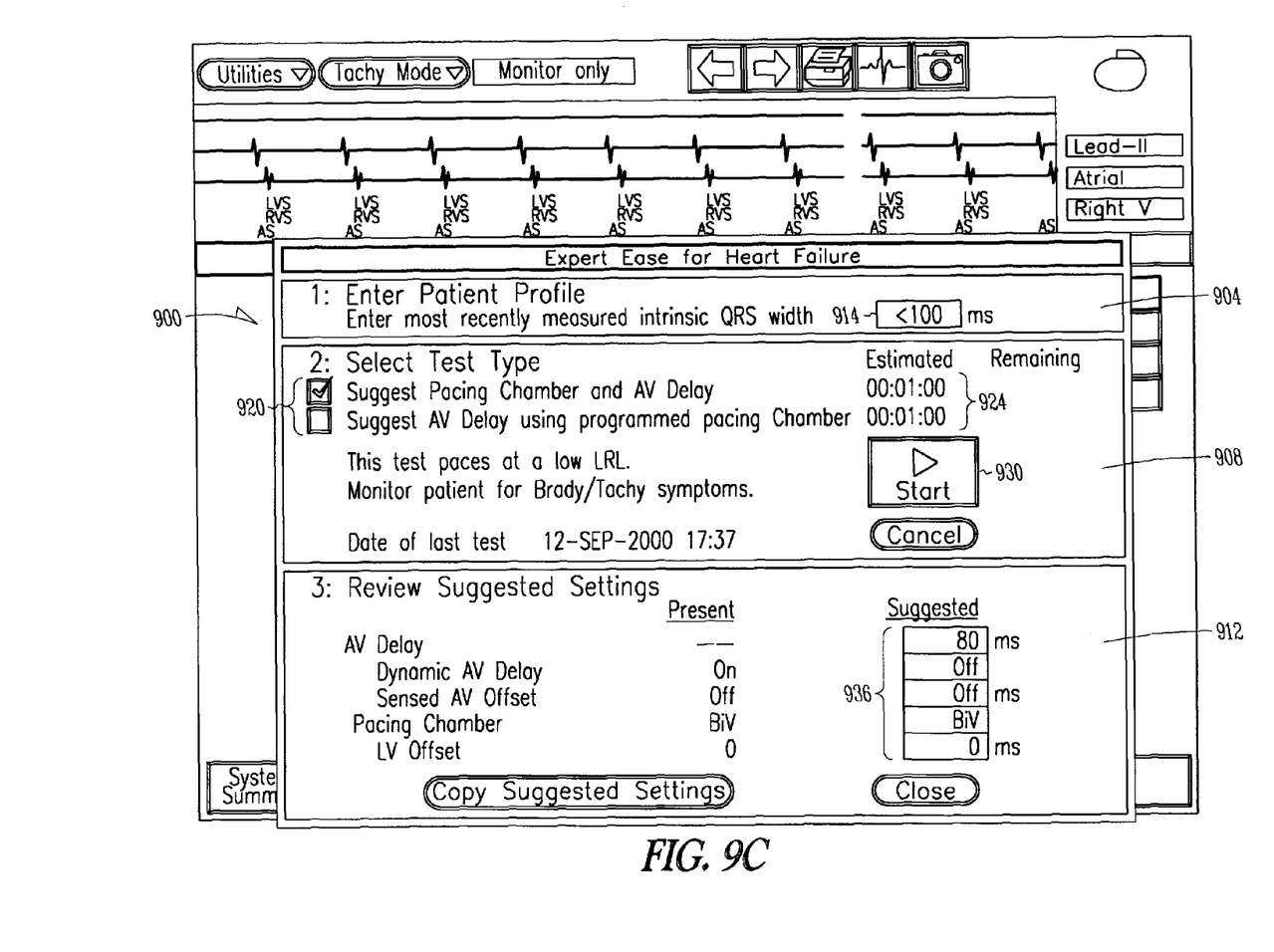
FIG. 9C is a schematic view of an interactive display screen of a medical device programmer according to one embodiment of the present subject matter.

FIGS. 9A, 9B, and 9C show examples of graphics display screen images for a medical device programmer, where each of the screen image represent a specific stages in the three stage process previously described. In FIG. 9A, there is shown a window 900 having three portions 904, 908 and 912. In the present example, screen portion 904 allows for patient profile information to be entered into the medical device programmer at input window 914. Patient profile information entered in 914 is the most recently measured intrinsic QRS width (in milliseconds), determined as previously described.

Once a value of the most recently measured intrinsic QRS width has been entered, the graphics display screen image changes to that seen in FIG. 9B. In the example in FIG. 9B, the first portion 904 has darkened as compared to FIG. 9A and displays the value of the most recently measured intrinsic QRS width in the input window 914. In FIG. 9B, screen portion 908 allows for the user to select at 920 between having the system suggest one or more ventricular pacing chamber and AV delay, or just providing these suggestions automatically if the permanently programmed or suggested ventricular pacing chamber is biventricular. Information relating to the number and position of the electrodes is provided through information downloaded from the implantable pulse generator (e.g., default settings downloaded from the device or a serial number of the implanted device used to identify location and number of electrodes) or from input through the programmer by the physician at a screen prior to 908. Once the desired information is requested, the programmer estimates the time to completion and displays this information on the display screen, as seen at 924. Once the desired test type has been selected, the user starts the test by means of a start button 930.

Other settings that could potentially be offered based on the QRS duration information include, but are not limited to, sensed AV delay offset, intrachamber ventricular pacing sites and/or atrial pacing sites. These sites are specific positions to locate the lead inside a chamber to achieve optimal therapy, as opposed to just provide a chamber. This position could be anterior, lateral, mid-lateral, posterior, or other any of a number of other positions within the heart.

When the test is complete, the graphics display screen image changes to that seen in FIG. 9C. In FIG. 9C, the third portion 912 of the window 900 is illuminated and contains the suggested settings for AV delay, ventricular pacing chamber and LV Offset (if applicable) at 936. Included in the suggested settings are dynamic AV delay which is always suggested as off to allow the suggested fixed AV delay to be used, and sensed AV delay offset which is always suggested to the same value as its permanent setting. To account for the sensed AV delay offset, the suggested AV delay is adjusted by the sensed AV delay offset amount so that when the sensed AV delay offset amount is subsequently subtracted from the suggested AV delay the resulting AV delay will be the originally suggested value of the AV delay.

In one embodiment, the suggested settings are either modified or kept as suggested by the programmer. When the user is finished, the suggested settings can then be copied into the change column for the permanent Brady/HF therapy settings and successively programmed into the electronic control circuitry of the implantable pulse generator as the permanent settings.

Implantable Pulse Generators

Figure 10:
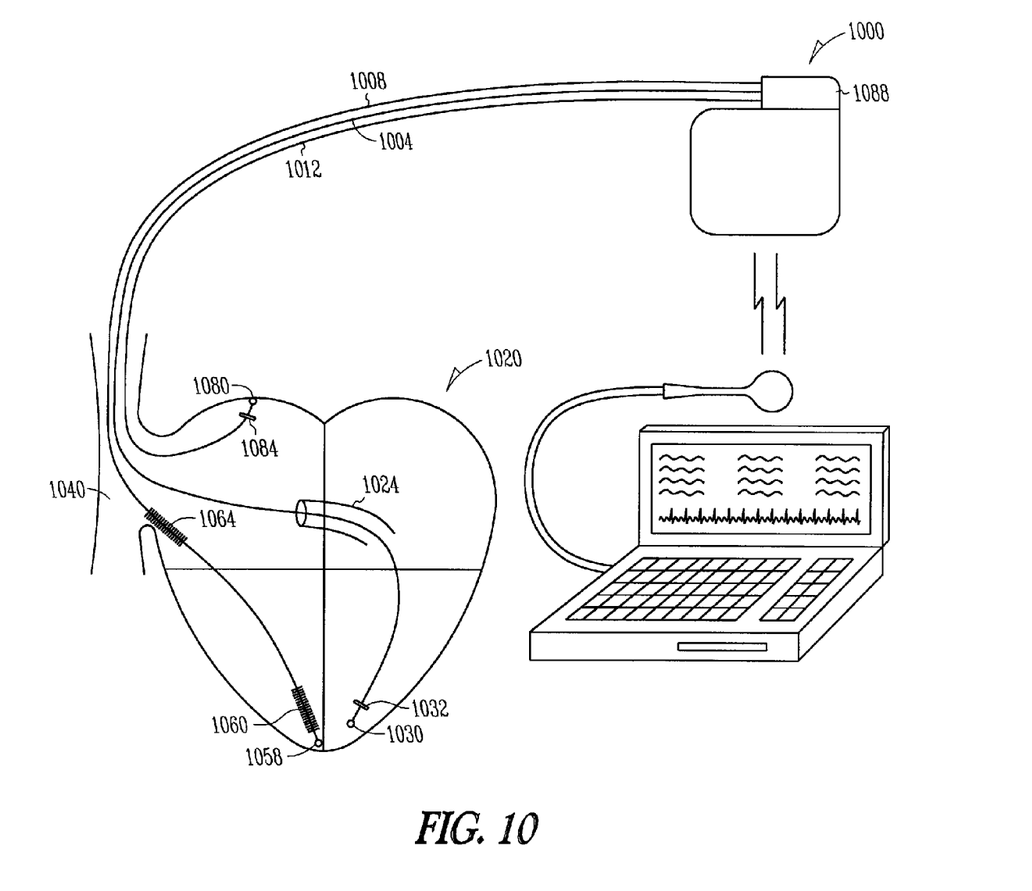
FIG. 10 is a schematic view of an implantable medical device and a heart, in which portions of the heart have been removed to show detail, according to one embodiment of the present subject matter.

FIG. 10 is a schematic drawing illustrating generally by way of example, but not by way of limitation, one embodiment of an implantable pulse generator 1000 coupled by leads 1004, 1008 and 1012 to a heart 1020. In one such embodiment, the implantable pulse generator 1000 provides biventricular coordination therapy to coordinate right ventricular and left ventricular contractions, such as for heart failure patients. FIG. 10 includes a left ventricular lead 1004, inserted through coronary sinus 1024 and into the great cardiac vein so that its electrodes, which include electrodes 1030 and 1032, are associated with left ventricle 1036 for sensing intrinsic heart signals from the left ventricle 1036 and providing one or more of coordination paces or defibrillation shocks. A right ventricular lead 1008 is also shown in FIG. 10, where the lead 1008 is inserted through the superior vena cava 1040 and the right atrium 1048 into the right ventricle 1052 so that its electrodes, which include electrodes 1058, 1060 and 1064, are associated with the right ventricle 1052 for sensing intrinsic heart signals from the right ventricle 1052 and providing one or more of coordination paces or defibrillation shocks. FIG. 10 also includes a right atrium lead 1012, where the right atrium lead 1012 is inserted through the superior vena cava 1040 into the right atrium 1048 so that its electrodes, which include electrodes 1080 and 1084, are associated with the right atrium 1048 for sensing intrinsic heart signals from the right atrium 1048 and providing one or more coordination paces shocks.

The implantable pulse generator 1000 further includes a connector block 1088 adapted to releasable couple leads 1004, 1008 and 1012 to the pulse generator and to couple the electrodes located on the leads to the electronic control circuitry located within the implantable pulse generator 1000. The electronic circuitry within the implantable pulse generator 1000 senses cardiac signals from the heart and provides electrical pulses, such as pacing and/or defibrillation pulses, under predetermined conditions of the heart 1020. The electronic circuitry also contains transmitting and receiving circuitry for communicating with an external medical device programmer, as previously described.

Although specific embodiments have been illustrated and described herein, it will be appreciated by those of ordinary skill in the art that any arrangement which is calculated to achieve the same purpose may be substituted for the specific embodiment shown. This application is intended to cover any adaptations or variations of the present invention. Therefore, it is intended that this invention be limited only by the claims and the equivalents thereof.

We claim:

1. A method, comprising:
    measuring PR interval durations;
    measuring a duration interval of a ventricular depolarization (QRS complex);
    measuring a timing relationship between the right and left ventricular depolarizations $R_L$ and $R_R$, where $R_L$ is a time at which a depolarization in the left ventricle occurred and $R_R$ is a time at which the depolarization in a right ventricle occurred;
    selecting an AV delay interval for delivering one or more ventricular pacing pulses based on at least first and second PR interval durations;
    selecting among ventricular pacing sites in which to provide pacing pulses based on the ventricular depolarization duration interval and the timing relationship between right and left ventricular depolarizations; and
    delivering ventricular pacing with the selected AV delay interval and the selected ventricular pacing site or sites.

2. The method of claim 1 further comprising selecting pacing in the left ventricle when the duration interval of the QRS complex is greater than or equal to 120 milliseconds and $R_L$ occurs later than $R_R$.

3. The method of claim 1 further comprising selecting pacing in both the left ventricle and the right ventricle when the duration interval of the QRS complex is greater than or equal to 120 milliseconds and $R_L$ occurs later than $R_R$.

4. The method of claim 1 further comprising selecting pacing in the right ventricle when the duration interval of the QRS complex is greater than or equal to 120 milliseconds and $R_R$ occurs later than $R_L$ or at the same time as $R_L$.

5. The method of claim 1 further comprising selecting an LV offset value for use in biventricular pacing based on the timing relationship between right and left ventricular depolarizations.

6. The method of claim 1 further comprising selecting an AV delay interval by computing a weighted average of a plurality of PR interval durations.

7. A system, comprising:
    means for measuring PR interval durations;
    means for measuring a duration interval of a ventricular depolarization (QRS complex);

means for measuring a timing relationship between the right and left ventricular depolarizations $R_L$ and $R_R$, where $R_L$ is a time at which a depolarization in the left ventricle occurred and $R_R$ is a time at which the depolarization in a right ventricle occurred;

means for selecting an AV delay interval for delivering one or more ventricular pacing pulses based on at least first and second PR interval durations;

means for selecting among ventricular pacing sites in which to provide pacing pulses based on the ventricular depolarization duration interval and the timing relationship between right and left ventricular depolarizations; and means for delivering ventricular pacing with the selected AV delay interval and the selected ventricular pacing site or sites.

8. The system of claim 7 further comprising means for selecting pacing in the left ventricle when the duration interval of the QRS complex is greater than or equal to 120 milliseconds and $R_L$ occurs later than $R_R$.

9. The system of claim 7 further comprising means for selecting pacing in both the left ventricle and the right ventricle when the duration interval of the QRS complex is greater than or equal to 120 milliseconds and $R_L$ occurs later than $R_R$.

10. The system of claim 7 further comprising means for selecting pacing in the right ventricle when the duration interval of the QRS complex is greater than or equal to 120 milliseconds and $R_R$ occurs later than $R_L$ or at the same time as $R_L$.

11. The system of claim 7 further comprising means for selecting an LV offset value for use in biventricular pacing based on the timing relationship between right and left ventricular depolarizations.

12. The system of claim 7 further comprising means for selecting an AV delay interval by computing a weighted average of a plurality of PR interval durations.

13. A system, comprising:
an external programmer:
an implantable pulse generator in communication with the external programmer;

wherein the implantable pulse generator is configured to measure PR interval durations, a duration interval of a ventricular depolarization (QRS complex), and a timing relationship between the right and left ventricular depolarizations $R_L$ and $R_R$, where $R_L$ is a time at which a depolarization in the left ventricle occurred and $R_R$ is a time at which the depolarization in a right ventricle occurred;

wherein the external programmer is configured to suggest an AV delay interval for use by the implantable pulse generator in delivering one or more ventricular pacing pulses based on at least first and second PR interval durations; and, wherein the external programmer is configured to suggest one or more ventricular pacing sites in which to provide pacing pulses based on the ventricular depolarization duration interval and the timing relationship between right and left ventricular depolarizations.

14. The system of claim 13 wherein the external programmer is configured to suggest pacing in the left ventricle when the duration interval of the QRS complex is greater than or equal to 120 milliseconds and $R_L$ occurs later than $R_R$.

15. The system of claim 13 wherein the external programmer is configured to suggest pacing in both the left ventricle and the right ventricle when the duration interval of the QRS complex is greater than or equal to 120 milliseconds and $R_L$ occurs later than $R_R$.

16. The system of claim 13 wherein the external programmer is configured to suggest pacing in the right ventricle when the duration interval of the QRS complex is greater than or equal to 120 milliseconds and $R_R$ occurs later than $R_L$ or at the same time as $R_L$.

17. The system of claim 13 wherein the external programmer is configured to suggest an LV offset value for use in biventricular pacing based on the timing relationship between right and left ventricular depolarizations.

18. The system of claim 13 wherein the external programmer is configured to suggest an AV delay interval by computing a weighted average of a plurality of PR interval durations.

* * * * *